United States Patent [19]
Ramsey, III

[11] Patent Number: 5,928,270
[45] Date of Patent: Jul. 27, 1999

[54] METHOD AND APPARATUS FOR INCREMENTAL CARDIOVERSION OR DEFIBRILLATION

[75] Inventor: Maynard Ramsey, III, Tampa, Fla.

[73] Assignee: CardioCommand, Inc., Tampa, Fla.

[21] Appl. No.: 08/982,765

[22] Filed: Dec. 2, 1997

[51] Int. Cl.$^6$ ..................................................... A61N 1/39
[52] U.S. Cl. .................................................... 607/5; 607/4
[58] Field of Search .................................... 607/4, 5, 124, 607/129, 46, 48

[56] References Cited

U.S. PATENT DOCUMENTS

| | | | |
|---|---|---|---|
| 4,708,145 | 11/1987 | Tacker, Jr. et al. | 607/5 |
| 4,969,463 | 11/1990 | Dahl et al. | 607/5 |
| 5,107,834 | 4/1992 | Ideker et al. | 607/5 |
| 5,184,620 | 2/1993 | Cudahy et al. | |
| 5,549,656 | 8/1996 | Reiss. | |
| 5,562,718 | 10/1996 | Palermo. | |
| 5,620,468 | 4/1997 | Mongeon et al. | |

OTHER PUBLICATIONS

J. Fields, "Special Electrode Device for Trans–Esophageal Cardioversion", *Digest of the 7th International Conference on Medical and Biological Engineering*, 1967, p. 77.
Y. Yamanouchi, "Transesophageal Low–Energy Synchronous Cardioversion of Atrial Flutter/Fibrillation In The Dog", *American Heart Journal*, Feb. 1992, pp. 417–420.
C. Yunchang, "Transesophageal Low–Energy Cardioversion in an Animal Model of Life–Threatening Tachyarrhythmias", *Circulation*, vol. 80, No. 5, Nov. 1989, pp. 1354–1359.
P. McKeown, "Esophageal Countershock: Anthropometric Determinants of Impedance", *Academic Emergency Medicine*, vol. 2/No. 1, Jan. 1995, pp. 63–68.
J. Montoyo, "Cardioversion of Tachycardias by Transesophageal Atrial Pacing", *The American Journal of Cardiology*, vol. 32, Jul. 1973, pp. 85–90.
E. McNally, Elective Countershock in Unanesthetized Patients With Use of an Esophageal Electrode, *Circulation*, vol. XXXIII, Jan. 1996.
R. Sweeney, "Characteristics of Multiple–Shock Defibrillation", *Journal of Cardiovascular Electrophysiology*, vol. 6, No. 2, Feb. 1995, pp. 89–102.
J. Wharton, "Cardiac Potential and Potential Gradient Fields Generated by Single, Combined, and Sequential Shocks During Ventricular Defibrillation", *Circulation*, vol. 85, No. 4, Apr. 1992, pp. 1510–1523.
Z. Csanadi, "Comparison of Single–Biphasic Versus Sequential–Biphasic Shocks on Defibrillation", *PACE*, vol. 20, Jun. 1997, pp. 1606–1612.

(List continued on next page.)

*Primary Examiner*—William E. Kamm
*Assistant Examiner*—Carl H. Layno
*Attorney, Agent, or Firm*—Gerstman, Ellis & McMillin, Ltd.

[57] ABSTRACT

A method is provided for cardioverting or defibrillating a patient's heart. A plurality of electrodes is positioned on a plurality of different locations on the patient. Different sets of the plurality of electrodes are pulsed with a plurality of pulses within a maximum time period of 200 milliseconds. By using multiple, relatively low energy shocks to different locations instead of a single large shock, there is significantly less trauma to the patient, and during cardioversion the use of anesthesia may be avoided.

42 Claims, 3 Drawing Sheets

OTHER PUBLICATIONS

I. Van Gelder, "Cardioversion of Atrial Fibrillation and Subsequent Maintenance of Sinus Rhythm", *PACE,* vol. 20, Oct. 1997, Part II, pp. 2675–2685.

A. Katz, "Bedside Termination of Sustained Ventricular Tachycardia by Transesophageal Atrial Pacing", *PACE,* vol. 15, Jun. 1992, pp. 849–853.

R. Sweeney, "Double–Pulse Defibrillation Using Pulse Separation Based on the Fibrillation Cycle Length", *Journal of Cardiovascular Electrophysiology,* vol. 5, No. 9, Sep. 1994, pp. 761–770.

H. Hsia, "Comparison of Simultaneous Versus Sequential Defibrillation Pulsing Techniques Using a Nonthoractomy System", *PACE,* vol. 17, Jul. 1994, pp. 1222–1230.

B. Baker, "Low Energy Internal Cardioversion for Atrial Fibrillation Resistant to External Cardioversion", *Journal of Cardiovascular Electrophysiology,* vol. 6, No. 1, Jan. 1995, pp. 44–47.

D. Keane, "Impact of Pulse Characteristics on Atrial Defibrillation Energy Requirements", PACE, vol. 17, May 1994, Part II, pp. 1048–1057.

R. Ammer, "Pain Threshold for Low Energy Intracardiac Cardioversion of Atrial Fibrillation with Low or No Sedation", *PACE,* vol. 20, Jan. 1997, Part II, pp. 230–236.

C. Alferness, "Lead Systems for Atrial Defibrillation", *PACE,* vol. 17, May 1994, Part II, pp. 1043–1047.

| Time (t) ms. | Shock Period | Cathode | Anode | Field | 1st Sequence Energy | Another Sequence Energy |
|---|---|---|---|---|---|---|
| 0 | 1 | E3 (E4) | E5 (S4) | P | 1.5 J | 4 J |
| 11 | 2 | S4 (S5) | E3 (E4) | P | 1.5 | 3 J |
|  |  | E2 | S5 | S | 1.0 | 2 J |
| 22 | 3 | E2 (E3,34) | L3 (L4) | P | 1.5 | 3 J |
|  |  | E1 | S5 | S | 2.0 | 4 J |
| 33 | 4 | R3 (R4) | E2 (E3, E4) | P | 2.0 | 5 J |
|  |  | S5 (S4) | E1 | S | 3.0 | 9 J |
|  |  |  |  |  | 12.5 J | 30 J |

P = PRIMARY FIELD GENERATOR

S = SUPPLEMENTAL FIELD GENERATOR ( ) = A CLONE OF THE PARENT ELECTRODE

Fig. 6

METHOD AND APPARATUS FOR INCREMENTAL CARDIOVERSION OR DEFIBRILLATION

FIELD OF THE INVENTION

The present invention concerns a novel method and apparatus for treating cardiac arrhythmias, and more particularly, a method and apparatus for cardioverting or defibrillating a patient using a novel stimulation technique.

BACKGROUND OF THE INVENTION

Prior art cardioversion and defibrillation methods typically require high energy shocks which may be extremely traumatic to the patient. A typical transthoracic cardioversion shock may have an energy range of between 80 joules and 200 joules. A typical transthoracic defibrillation shock may have an energy range between 100 joules and 400 joules. Both shocks ordinarily derive from an electrical pulse, either monophasic or multiphasic, having a duration between about 2 milliseconds and 10 milliseconds. Ordinarily such shocks require that a conscious patient be anesthetized.

I have discovered a method and apparatus for cardioverting or defibrillating a patient's heart, without requiring that the patient be anesthetized. It is, therefore, an object of the present invention to provide a method and apparatus for cardioverting or defibrillating a patient, which are significantly less traumatic to the patient and do not require the use of anesthesia on a conscious patient.

Another object of the present invention is to provide a method and apparatus for cardioverting or defibrillating a patient, which method and apparatus are relatively simple in operation yet produce highly effective results.

Other objects and advantages of the present invention will become apparent as the description proceeds.

SUMMARY OF THE INVENTION

In accordance with an illustrative embodiment of the invention, a method of cardioverting or defibrillating a patient is provided, comprising the steps of positioning a plurality of electrodes on a plurality of different locations on the patient, and pulsing different electrodes of the plurality of electrodes over a time period that does not exceed 200 milliseconds using at least three spaced pulses during the time period.

As used in the specification and claims, the term "on the patient" includes on the skin or outer surface of the patient and/or within the patient's body, including but not limited to the patient's esophagus, or stomach, the patient's heart and/or anywhere else from where transmission of energy to the heart can be accomplished.

In another embodiment of the invention, a method for cardioverting or defibrillating a patient is provided in which different sets of the plurality of electrodes are pulsed with a plurality of pulses within a maximum time period of 200 milliseconds.

In accordance with an illustrative embodiment of the invention, a patient is cardioverted or defibrillated by positioning a plurality of electrodes on a plurality of different locations on the patient. A first set of the plurality of electrodes is pulsed at a first time period. A second set of the plurality of electrodes is pulsed at a second time period. At least one electrode of the second set is different from an electrode of the first set. The first time period and the second time period have a total maximum time of 200 milliseconds.

In the illustrative embodiment, the pulses are multiphasic pulses and the step of pulsing to the second set comprises providing a plurality of multiphasic pulses that differ from the multiphasic pulses to the first set. At least one of the sets comprises a plurality of cloned electrodes forming an anode and a plurality of cloned electrodes forming a cathode. In the illustrative embodiment, the first time period commences at the patient's R-wave.

In the illustrative form of the invention, the step of pulsing the first set comprises providing a pulse to a primary set of electrodes and providing a pulse to a supplemental set of electrodes. Likewise, the step of pulsing the second set comprises providing a pulse to a primary set of electrodes and providing a pulse to a supplement set of electrodes. Additional sets of electrodes may be pulsed at subsequent time periods, with all of the time periods having a total maximum time of 200 milliseconds.

Thus in accordance with an embodiment of the present invention, repeated shocks are delivered, in rapid sequence, from single or multiple electrode geometries. Shocks of less energy than prior art shocks are delivered within 200 milliseconds from multiple sets of electrodes. Each set is designed to stimulate or to extend the refractory period of a portion of the heart, recognizing that different electrode sets are advantageously positioned to best stimulate different portions of the heart.

The advantage of the aforesaid incremental cardioversion or incremental defibrillation is that the energy of each shock, whether monophasic, biphasic or triphasic and whether single or repetitive, will be less than that required to stimulate the heart (or the critical mass) with a single or serial shocks from a single geometry of stimulating electrodes. The desired result is thus achieved by a series of smaller shocks that are less injurious or less traumatic to the heart or the esophagus or to the skin and are less painful to the patient. The reduction of pain by spreading the energy over a relatively long time period in contrast to the prior art in which the energy is delivered in a larger dose over a much shorter time period, permits the cardioversion of atrial fibrillation and flutter and ventricular tachycardia and fibrillation without the requirement of anesthesia in conscious patients.

In accordance with an illustrative embodiment of the invention utilizing the principles of incremental cardioversion or incremental defibrillation, an apparatus is provided which comprises a plurality of electrodes for positioning on a plurality of different locations on the patient. Means are provided for pulsing different electrodes of the plurality of electrodes over a time period that does not exceed 200 milliseconds without an intervening R-wave using at least three spaced pulses during that time period.

In one embodiment, means are provided for pulsing different sets of the plurality of electrodes with a plurality of pulses within the maximum time period of 120 milliseconds without an intervening R-wave.

A more detailed explanation of the invention is provided in the following description and claims, and is illustrated in the accompanying drawings.

DETAILED DESCRIPTION OF THE INVENTION

FIG. 6 is a timing chart of a pulse sequence according to the principles of the present invention.

DETAILED DESCRIPTION OF THE ILLUSTRATIVE EMBODIMENTS

Figure 1:
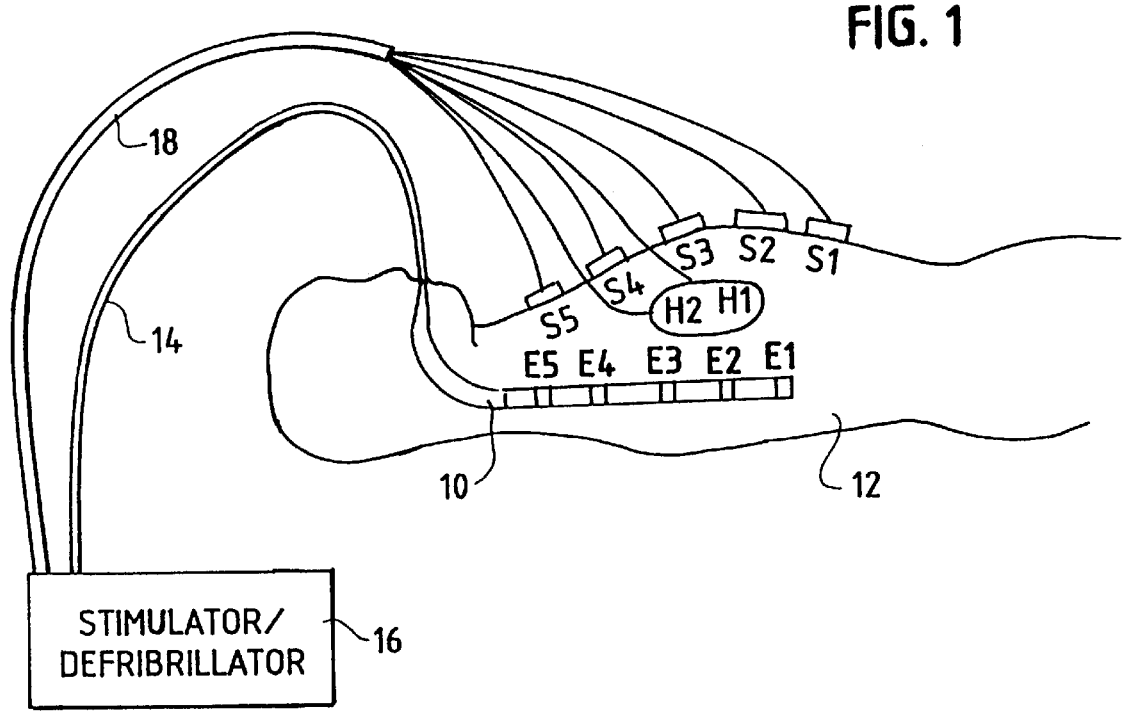
FIG. 1 is a fragmentary diagrammatic view of a patient with an esophageal catheter inserted and positioned adjacent a posterior heart surface and with epidermal electrodes and cardiac electrodes connected to a stimulator/defibrillator in accordance with the principles of the present invention.

Referring to FIG. 1, an esophageal catheter 10 has been introduced into the esophagus of a patient 12. Catheter 10 may be constructed in accordance with Bilof et al. U.S. Pat. No. 5,191,885, issued Mar. 9, 1993, the disclosure of which is incorporated herein by reference. Esophageal catheter 10 includes spaced esophageal electrodes E1, E2, E3, E4 and E5 which are electrically connected via cable 14 to stimulator/defibrillator 16 which includes a suitable current or voltage source and pulse generator for providing cardioverting and/or defibrillating pulses.

Although an esophageal catheter 10 is illustrated, it is to be understood that in addition to a catheter being positioned in the esophagus, the catheter could be positioned in the stomach, the trachea, the vascular system including within the heart, on the heart or around the heart, either internally or on the skin or in the subcutaneous tissue of the chest, neck, abdomen, limbs, etc. In FIG. 1, intracardiac electrodes H1 and H2 are shown connected to the patient's heart.

Figure 2:
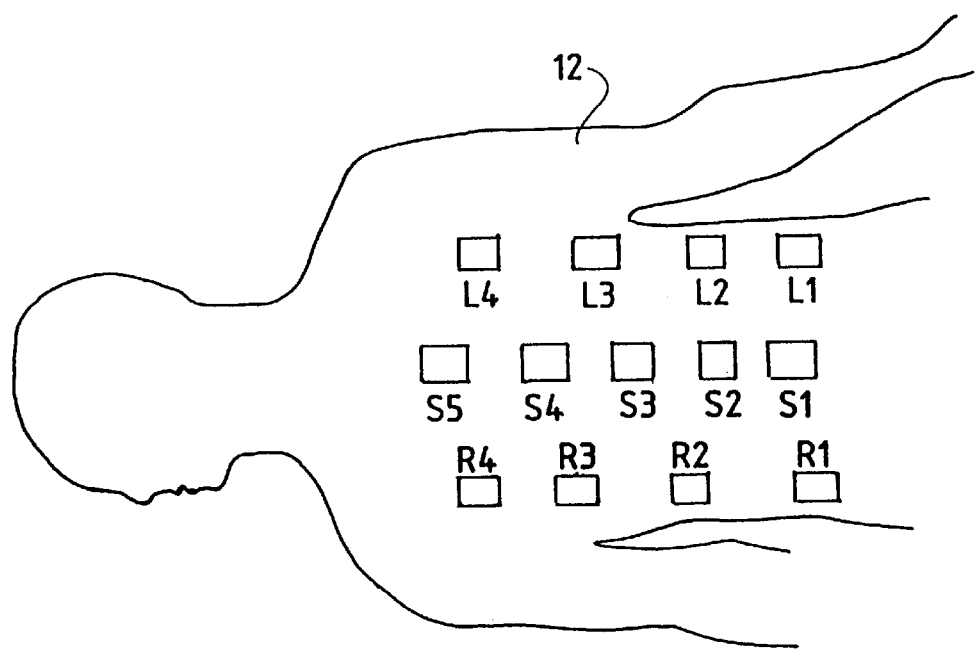
FIG. 2 is a fragmentary diagrammatic view of a patient with epidermal electrodes positioned in accordance with the principles of the present invention.

In the illustrative embodiment as illustrated in FIGS. 1 and 2, surface or epidermal electrodes are also positioned on the patient's skin. FIGS. 1 and 2 show sternum electrodes S1, S2, S3, S4 and S5, and FIG. 2 shows left lateral electrodes L1, L2, L3 and L4 and right lateral electrodes, R1, R2, R3 and R4. Many of these electrodes are cloned; that is, cloned electrodes comprise electrodes that are electrically connected together to act as a single electrically conductive unit. Heart electrodes H1 and H2 and epidermal electrodes S1–S5, L1–L4 and R1–R4 are connected to stimulator defibrillator 14 via cable 18.

Figure 3:
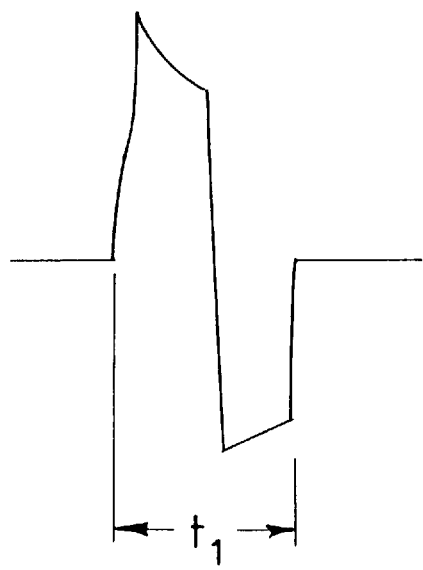
FIG. 3 is a prior art biphasic waveform.

An illustrative example of the use of the present invention is in cardioversion or defibrillating of an unanesthetized patient in atrial fibrillation. In the prior art, ordinarily a conscious patient would have to be anesthetized in order to be cardioverted or defibrillated. This is because in the prior art a typical cardioverting pulse or defibrillating pulse provides a high energy shock over a relatively short period of time. Referring to FIG. 3, for example, a prior art biphasic defibrillating pulse having an energy of 50 joules is issued in a time period $t_1$ of between 2 milliseconds and 10 milliseconds. In the present invention, pulses utilized for cardioversion or defibrillation are significantly smaller, having reduced amplitudes, and repeat over a substantially longer period of time. For example, in a 100 millisecond time interval, 10 spaced pulses may be utilized. Each of the pulses may be monophasic or biphasic or triphasic and each pulse could have an energy of between 0.04 joule and 40 joules.

Figure 5:
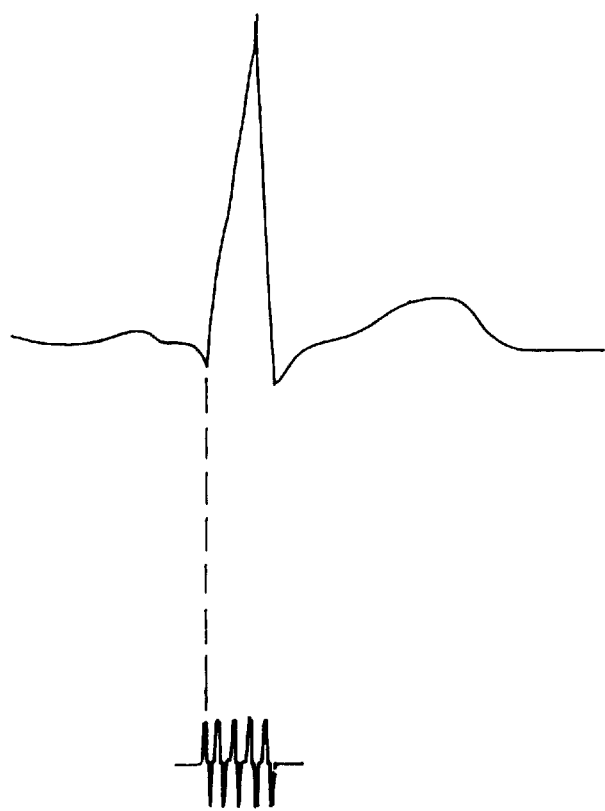
FIG. 5 is a view of a cardiac waveform and pulses generated in accordance with the principles of an embodiment of the present invention.
Figure 4:
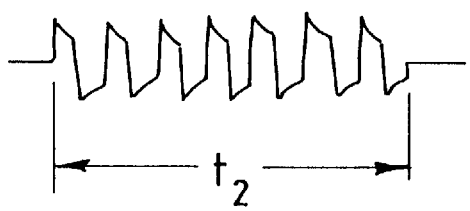
FIG. 4 is a view of biphasic pulses in accordance with the embodiment of the present invention.

Referring to FIG. 4, the total time period $t_2$ for the series of pulses is no more than 200 milliseconds, and is preferably between 40 milliseconds and 200 milliseconds. As illustrated in FIG. 5, in a preferred embodiment the defibrillating pulses begin at about the onset of the R-wave, and by terminating within 200 milliseconds, the T-wave is avoided.

The importance of avoiding the T-wave cannot be overemphasized, because a shock occurring during the T-wave portion of the cycle may cause fibrillation of the heart. Thus in accordance with the present invention, the ECG signal of the heart is sensed and the series of pulses begin and end at a time which avoids the T-wave and only at a time during the expansion and contraction cycle of the heartbeat which would not cause fibrillation of the heart. For additional safety it is preferred that the series of pulses begin and end only during the electrical depolarization of the ventricles if atrial fibrillation is being cardioverted.

Alternatively, in order to avoid the T-wave, instead of beginning the defibrillating pulses at about the onset of the R-wave, the stimulus sequence is begun at least 300 milliseconds after the R-wave.

The present invention uses a multi-vector system in which the stimulation occurs at various locations on the patient. The first vector receiving the first pulse could be a pair of electrodes from the sternum to a single or to multiple electrodes in the esophagus. The second vector receiving the next pulse could be from two or more lateral epidermal electrodes and two or more posterior epidermal electrodes on the subject's back. Another vector could be from one esophagus electrode to another esophagus electrode, etc. Thus with each of the consecutive or overlapping pulses, if different vectors are used each pulse would depolarize a different area of the myocardium. While two or more consecutive pulses could depolarize the same area, in the illustrative embodiment there is a change of vector for at least some of the pulses. The basic purpose is to aim the current flow in different directions to achieve depolarization of a majority of the myocardium, whether ventricular or atrial or both.

In another embodiment, a single electrode could be used in the esophagus with multiple cloned electrodes on the skin surface, using multiple pulses while using a constant current vector for all of the pulses. In this manner, the locations remain constant but are stimulated repeatedly and with a variety of pulse strengths and shapes until cardioversion is successful.

Each pulse does not necessarily have the same energy as the other pulses—it depends on the vector. Some vectors may require far more energy than other vectors. By spreading the energy over a substantially longer duration than the 2–10 milliseconds of the prior art, with a significantly lower amplitude, there is much less trauma to the patient. The method of the present invention can be used for other than defibrillating or cardioverting atrial fibrillation; it can also be used to terminate atrial flutter, ventricular tachycardia, ventricular fibrillation, etc. In patients who are unsedated, sedated or anesthetized.

Pretreatment with anti-arrhythmic drugs to lower the defibrillation threshold may be useful. Further, some overlap of the shocks might be useful in reducing the energy or time required to defibrillate.

By utilizing the present invention, the field generation is spread over a broad geometry and over greater time than the prior art. A pair of electrodes at one location may use 60 percent of the energy while a pair of electrodes at another location may use 40 percent of the energy. In this manner, 100 percent of the energy is spread out over a broader geometry, using more electrodes. The advantage of this is that the stimulation to a single location such as the esophagus, is less. This will be significantly more comfortable than a single or more powerful energy blast from a single set of electrodes. This reduces the amount of current that flows through any given set of stimulus electrodes, in contrast to the prior art where a single set of stimulus electrodes is used for depolarization resulting in significant discomfort and requiring anesthesia under certain conditions.

The stimulus set of electrodes, including their geometry, their clones and the strength of stimulation, comprises a stimulation set. The stimulation set which provides the highest field in the heart is the primary stimulation set. The stimulation set that provides a lesser field is the supplemental set of electrodes which provides a supplemental field. The total field is the sum of the two individual fields.

In an example atrial defibrillation sequence, although no limitation is intended, the ventricle is captured by pacing electrodes E2 and E3 at a cycle length that is equal to about 10–20 percent less than the fastest cycle length that was measured for 60 seconds prior to the atrial defibrillation attempt. Thereafter, capture is verified for three to five seconds. If capture is not achieved, the pacing stimulus is revised and capture is again verified for three to five seconds. Once capture is verified, the defibrillating pulses are delivered in a rapid sequence commencing with the patient's R-wave. This pacing is useful in patients with irregular rhythm and is not always required.

The timing chart of FIG. 6 shows an example of non-invasive, low energy defibrillation in which four sequential shocks are issued over a total time period that is slightly over 33 milliseconds. As used herein, the term "non-invasive" means that nothing is introduced into the patient's arteries or veins and/or that surgery is not required. A similar cardioversion scheme could be executed using invasive and non-invasive electrodes for either atrial or ventricular defibrillation.

Referring to FIG. 6, the first shock commences at time t=0 which is approximately at the commencement of the patient's R-wave. For the first shock, the cathode comprises cloned electrodes E3 and E4 (both of which are esophageal electrodes). The anode comprises cloned electrodes E5 and S4. As illustrated in FIGS. 1 and 2, E5 is an esophageal electrode and S4 is an epidermal electrode adjacent the sternum.

Stimulator/defibrillator 16 provides at least two channels of cardiac defibrillation. The channels can be simultaneously fired or sequentially fired. With the first pulse, since the cathode electrodes are cloned and the anode electrodes are cloned, there is only a primary field with the primary set receiving 1.5 joules.

The second shock commences at t=11 milliseconds. With the second shock, the primary stimulation set comprises cloned electrodes S4 and S5 as the cathode and cloned electrodes E3 and E4 as the anode. The energy for the primary set is 1.5 joules. The supplemental set comprises cathode electrode E2 and anode electrode S5, receiving an energy of 1 joule, thus a total energy of 2.5 joules.

The third shock commences at time t=22 milliseconds. The primary stimulation set comprises cloned electrodes E2, E3 and E4 as the cathode and cloned electrodes L3 and L4 as the anode. The total energy received by the primary stimulation set is 1.5 joules. The supplemental stimulation set for the third shock is electrode E1 as the cathode and electrode S5 as the anode, with an energy received by the supplemental set of 2 joules; 3.5 joules total.

A fourth shock is issued at time t=33 milliseconds. For the fourth shock, the primary stimulation set comprises cloned electrodes R3 and R4 forming the cathode and cloned electrodes E2, E3 and E4 forming the anode. The primary stimulation set receives an energy of 2 joules. The supplemental set electrodes comprises electrodes S5, S4 cloned as the cathode and electrode E1 as the anode, and receives an energy of 3 joules; 5 joules total.

As shown, the first sequence delivers 12.5 joules total over 33 milliseconds. This average energy density of 12.5 joules/33 milliseconds is equal to 0.28 joules/millisecond. In prior art defibrillation methods, typical energy densities are on the order of 200 joules/2 milliseconds, i.e. 100 joules/millisecond which is clearly more likely to cause severe discomfort and tissue damage.

If the first sequence is not successful at cardioversion, a next sequence with greater energy and/or different stimulation geometry vectors is used. For example, referring to FIG. 6, in the second sequence with the first pulse, there is only a primary field with a primary set receiving four joules. At t=11 milliseconds, there is a second shock with the energy for the primary set being 3 joules and the energy for the supplemental set being 2 joules. At t=22 milliseconds, the energy received by the primary stimulation set is 3 joules and the supplemental stimulation set receives a total energy of 4 joules. At t=33 milliseconds (the fourth shock) the primary stimulation set receives an energy of 5 joules and the supplemental set receives an energy of 9 joules. It can be seen that the second sequence delivers a total of 30 joules over 33 milliseconds. This provides an average energy density of 0.91 joules per millisecond. It is to be understood that successive sequences may utilize greater, lesser or equal energy stimulation and similar or different stimulation geometry vectors. Further, the sequence and the timing and the repetition rates may be programmable by the physician. Preferably, different sequences are used until atrial or ventricular defibrillation is successful.

The pulse issued during each shock period could be a monophasic pulse, a biphasic pulse, or a triphasic pulse, or a number of monophasic or multiphasic pulses could issue during each shock period as desired. In addition to shock periods 1, 2, 3 and 4, additional shock time periods 5, 6, 7, etc. could be utilized so long as the pulses terminate within 200 milliseconds in order to avoid the T-wave. Most importantly, the total shock time period should be substantially less than the time from the commencement of the R-wave to the commencement of the T-wave. The shock sequence may be repeated exactly (or varied) on successive heart beats.

The method of the present invention is particularly useful in connection with cardioverting atrial fibrillation. It has been found that to entrain a portion of the fibrillating atrium, strong pacing of that portion will likely cause that area to follow the pacing commands. In this manner, a small portion of the atrium is captured and this will reduce some of the cardiac muscle that is involved in the fibrillation. Thus in an embodiment of the present invention, to reduce total energy during cardioversion of atrial fibrillation, the atrium is paced from the esophagus and/or from the heart directly. It is preferred that rapid atrial pacing of either subthreshold or super threshold intensity and timing be used. Without discontinuing the pacing, a cardioversion or defibrillation sequence is commenced at the beginning of an R-wave using a multiple number of relatively low intensity shocks in accordance with the FIG. 6 example, discussed above. In some cases, the esophageal atrial pacing will be synchronous or phased with direct cardiac stimulation from an intracardiac or epicardial electrode.

In the event the FIG. 6 example is unsuccessful, another multi-shock low energy sequence may be used. Various different electrode configurations could be employed, including the use of intracardiac electrodes.

It can be seen that the present invention utilizes repeated, rapidly sequenced pulses from single or multiple electrode geometries, using pulses each having less energy over a much longer period of time than the high energy pulses used in prior art defibrillation over a relatively short period of time. Advantageously, by using the present invention there is less potential of injury to the heart or to the esophagus or the skin and less pain to the patient, enabling conscious patients to be treated without anesthesia. In accordance with the present invention, the apparatus can be programmed to automatically pace or cardiovert the subject upon the detected occurrence of a rhythm to be treated. Further, the atrium may be continuously stimulated at low enough energy so as not to stimulate the ventricle, thus effecting cardioversion of the atrium by providing enough energy to capture the atrium but not stimulate the ventricle.

Although illustrative embodiments of the invention have been shown and described, it is to be understood that various modifications and substitutions may be made by those skilled in the art without departing from the spirit and scope of the present invention.

What is claimed is:

1. A method for cardioverting or defibrillating a patient, comprising the steps of:

positioning a plurality of electrodes on a plurality of different locations on the patient; and pulsing different electrodes of said plurality of electrodes over a time period that does not exceed 200 milliseconds using at least three pulses during said time period.

2. A method of non-invasive cardioverting or defibrillating a patient, comprising the steps of:

positioning a plurality of non-invasive electrodes on a plurality of different locations on the patient;

pulsing different sets of said plurality of non-invasive electrodes with a plurality of pulses within a maximum time period of 200 milliseconds.

3. Apparatus for cardioverting or defibrillating a patient, which comprises:

a plurality of electrodes for positioning on a plurality of different locations on the patient including a first set of electrodes comprising at least one of a surface electrode and an esophageal electrode; and a second set of electrodes;

means for pulsing said first set of said plurality of electrodes at a first time period;

means for pulsing said second set of said plurality of electrodes at a second time period;

at least one electrode of said second set being different from one electrode of said first set;

said first time period and said second time period having a total time that does not exceed 200 milliseconds.

4. A method for cardioverting or defibrillating a patient, comprising the steps of:

positioning a plurality of electrodes on a plurality of different locations on the patient including a first set of electrodes comprising at least one of a surface electrode and an esophageal electrode, and a second set of electrodes;

pulsing said first set of said plurality of electrodes at a first time period;

pulsing said second set of said plurality of electrodes at a second time period;

at least one electrode of said second set being different from one electrode of said first set;

said first time period and said second time period having a total time that does not exceed 200 milliseconds.

5. A method as defined in claim 4, in which said step of pulsing said first set comprises providing a pulse to a primary set of electrodes and providing a pulse to a supplemental set of electrodes.

6. A method as defined in claim 5, in which said steps of providing pulses comprises providing multiphasic pulses.

7. A method as defined in claim 4, in which said step of pulsing said second set comprises providing a pulse that differs from the pulse to said first set.

8. A method as defined in claim 4, in which at least one of said sets comprises a plurality of cloned electrodes forming an anode and a plurality of cloned electrodes forming a cathode.

9. A method as defined in claim 4, in which said first time period commences at the patient's R-wave.

10. A method as defined in claim 4, including locating a plurality of electrodes in the esophagus via an esophageal catheter.

11. A method as defined in claim 4, including using epidermal electrodes for at least some of said plurality of electrodes.

12. A method as defined in claim 4, including using intracardiac electrodes for at least some of said plurality of electrodes.

13. A method for cardioverting or defibrillating a patient, comprising the steps of:

positioning a plurality of electrodes on a plurality of different locations on the patient;

providing a plurality of spaced multiphasic pulses to a first set of said plurality of electrodes at a first time period;

providing a plurality of spaced multiphasic pulses to a second set of said plurality of electrodes at a second time period;

said plurality of pulses provided to said second set of plurality of electrodes differing from the pulses to said first set of said plurality of electrodes;

at least one electrode of said second set being different from an electrode of said second set;

said first time period commencing at the patient's R-wave with said first time period and said second time period having a total time that does not exceed 200 milliseconds.

14. A method as defined in claim 13, in which at least one of said sets comprises a plurality of cloned electrodes forming an anode and a plurality of cloned electrodes forming a cathode.

15. Apparatus for non-invasive cardioverting or defibrillating a patient, which comprises:

a plurality of non-invasive electrodes for positioning on a plurality of different locations on the patient;

means for pulsing different sets of said plurality of non-invasive electrodes with a plurality of pulses within a time period that does not exceed 200 milliseconds.

16. A method for cardioverting atrial fibrillation, which comprises the steps of:

positioning a plurality of electrodes on a plurality of different locations on the patient;

pacing the atrium rapidly; and without discontinuing the pacing, pulsing different sets of said plurality of electrodes with a plurality of pulses within a time period that does not exceed 200 milliseconds, with said pulsing step commencing at the beginning of an R-wave.

17. A method as defined in claim 16 in which the pacing step comprises pacing the atrium from the esophagus at one of subthreshold and superthreshold intensity.

18. A method for cardioverting or defibrillating a patient, comprising the steps of:
    positioning a plurality of electrodes on a plurality of different locations on the patient; and
    pulsing different electrodes of said plurality of electrodes over a time period during the cycle of the heartbeat which would not cause fibrillation of the heart, using at least three pulses during said time period.

19. A method of non-invasive cardioverting or defibrillating a patient, comprising the steps of:
    positioning a plurality of non-invasive electrodes on a plurality of different locations on the patient;
    sensing the ECG signal of the heart;
    pulsing different sets of said plurality of non-invasive electrodes with a plurality of pulses within a time period during the cycle of the heartbeat which would not cause fibrillation of the ventricle.

20. A method as defined in claim 19 in which the plurality of pulses occur only during the contraction cycle of the heartbeat.

21. A method as defined in claim 19, including the step of beginning the stimulus sequence at least 300 milliseconds after the R-wave.

22. A method as defined in claim 19, in which the sequence and the timing and the repetition rates of the stimulating pulses are programmable by the physician or patient.

23. A method as defined in claim 19, in which the pulsing step is automatically commenced upon the detected occurrence of a rhythm to be treated.

24. A method as defined in claim 19, including the step of providing enough energy to capture the atrium but not stimulate the ventricle, whereby cardioversion of the atrium is achieved without stimulating the ventricle.

25. A method of cardioverting or defibrillating a patient, comprising the steps of:
    positioning a plurality of electrodes on plurality of different locations on the patient;
    sensing the ECG signal of the heart; and
    pulsing different sets of said plurality of electrodes with a plurality of pulses that are of such strength and geometry as to not fibrillate the ventricle.

26. A method of cardioverting or defibrillating a patient, comprising the steps of:
    positioning a plurality of electrodes on a plurality of different locations on the patient;
    sensing the ECG signal of the heart; and
    pulsing different sets of said plurality of electrodes with a plurality of pulses, with said pulses providing enough energy to capture the atrium but not stimulate the ventricle, whereby cardioversion of the atrium is achieved without stimulating the ventricle.

27. A method as defined in claim 26, said plurality of electrodes defining one or more non-invasive electrodes.

28. A method as defined in claim 26, said plurality of electrodes defining one or more invasive electrodes.

29. A method of cardioverting or defibrillating a patient, comprising the steps of:
    positioning a plurality of electrodes on a plurality of different location on the patient;
    sensing the ECG signal of the heart;
    if an arrhythmia to be treated other than ventricular fibrillation is detected, then pulsing different sets of said plurality of electrodes with a plurality of pulses within a time period during the cycle of the heart beat which would not cause fibrillation of the heart; and
    if ventricular fibrillation is detected, then pulsing said different sets of electrodes with a plurality of pulses without a time period synchronization restriction.

30. A method as defined in claim 29, said plurality of electrodes defining one or more invasive electrodes.

31. A method as defined in claim 29, said plurality of electrodes defining one or more non-invasive electrodes.

32. A method of non-invasive cardioverting or defibrillating a patient, comprising the steps of:
    positioning a plurality of non-invasive electrodes on a plurality of different locations on the patient;
    sensing the ECG signal of the heart;
    detecting a rhythm to be treated;
    in response to said detecting step, pulsing different sets of said plurality of non-invasive electrodes with a plurality of pulses within a time period during the cycle of the heartbeat which would not cause fibrillation of the heart.

33. A method as defined in claim 32 in which if ventricular fibrillation is detected, then pulsing said different sets of non-invasive electrodes with a plurality of pulses without a time period synchronization restriction.

34. Apparatus for cardioverting or defibrillating a patient, which comprises:
    a plurality of electrodes for positioning on a plurality of different locations on the patient;
    means for pulsing a first set of said plurality of electrodes at a first time period;
    means for pulsing a second set of said plurality of electrodes at a second time period;
    means for pulsing a third set of said plurality of electrodes at a third time period;
    at least one electrode of each set being different from an electrode of the other sets;
    said first time period and said second time period having a total time that does not exceed 200 milliseconds.

35. A method for cardioverting or defibrillating a patient, comprising the steps of:
    positioning a plurality of electrodes on a plurality of different locations on the patient;
    pulsing a first set of said plurality of electrodes at a first time period;
    pulsing a second set of said plurality of electrodes at a second time period;
    pulsing a third set of said plurality of electrodes at a third time period;
    at least one electrode of each set being different from an electrode of the other sets;
    said first, second and third time periods having a total time that does not exceed 200 milliseconds.

36. A method as defined in claim 1, in which at least one of said electrodes is an epidermal electrode.

37. A method as defined in claim 1, in which at least one of said electrodes is an esophageal electrode.

38. A method as defined in claim 1, in which at least one of said electrodes is an intracardiac electrode.

39. A method as defined in claim 2, in which said pulsing step comprises pulsing with said plurality of pulses within a time period that is between 10 milliseconds and 200 milliseconds.

40. A method for cardioverting atrial fibrillation, which comprises the steps of:

positioning a plurality of electrodes on a plurality of different locations on the patient;

stimulating the atrium rapidly; and without discontinuing the stimulating, pulsing different sets of said plurality of electrodes with a plurality of pulses within a time period that does not exceed 200 milliseconds, with said pulsing step commencing at the beginning of an R-wave.

41. Apparatus as defined in claim 15, in which at least one of said non-invasive electrodes is an esophageal electrode.

42. Apparatus as defined in claim 15, in which at least one of said non-invasive electrodes is an epidermal electrode.

* * * * *